United States Patent [19]

Kaltenbach

[11] Patent Number: 5,211,654
[45] Date of Patent: May 18, 1993

[54] CATHETER WITH EXPANSIBLE DISTAL END

[76] Inventor: Martin Kaltenbach, Falltorweg 8, Dreieich-Buchschlag, Fed. Rep. of Germany

[21] Appl. No.: 713,398

[22] Filed: Jun. 10, 1991

[30] Foreign Application Priority Data

Jun. 9, 1990 [DE] Fed. Rep. of Germany ....... 4018525

[51] Int. Cl.⁵ ............................................. A61M 29/02
[52] U.S. Cl. ..................................... 606/191; 606/194
[58] Field of Search ................. 604/96, 101, 103, 104; 606/191, 192, 194, 195, 198; 623/1

[56] References Cited

U.S. PATENT DOCUMENTS

| | | |
|---|---|---|
| 1,690,995 | 11/1928 | Pratt . |
| 3,045,677 | 7/1962 | Wallace ................................. 604/101 |
| 4,702,252 | 10/1987 | Brooks et al. ....................... 606/195 |
| 4,723,549 | 2/1988 | Wholey et al. . |
| 4,793,359 | 12/1988 | Sharrow ................................ 128/658 |
| 4,796,629 | 1/1989 | Grayzel ................................... 604/93 |
| 4,819,751 | 4/1989 | Shimada et al. ..................... 604/104 |
| 5,100,429 | 3/1992 | Sinofsky et al. ..................... 606/195 |
| 5,116,318 | 5/1992 | Hillstead ............................... 604/96 |

FOREIGN PATENT DOCUMENTS

| | | |
|---|---|---|
| 0206553 | 12/1986 | European Pat. Off. . |
| 0246998 | 11/1987 | European Pat. Off. . |
| 3902364 | 8/1989 | Fed. Rep. of Germany . |
| 1547328 | 6/1979 | United Kingdom . |

*Primary Examiner*—John D. Yasko
*Assistant Examiner*—Anthony Gutowski
*Attorney, Agent, or Firm*—Peter K. Kontler

[57] ABSTRACT

A catheter for the opening of occlusions in blood vessels and for similar purposes has a distal end with a one-piece or composite sleeve which can be inserted into an occlusion and thereupon expanded by a balloon or a spring. The sleeve is sufficiently stiff to resist localized deformation by hard regions of an occlusion, and such sleeve is withdrawn from the blood vessel when the opening step is completed. The sleeve can constitute a scroll, a longitudinally slotted hose or a combination of a scroll or hose with an elastic jacket which tends to reduce the diameter of the scroll or hose.

9 Claims, 6 Drawing Sheets

CATHETER WITH EXPANSIBLE DISTAL END

BACKGROUND OF THE INVENTION

The invention relates to improvements in catheters in general, and more particularly to improvements in catheters with expansible distal ends.

Catheters with expansible distal ends are used to open an occlusion (stenosis) in a blood vessel or in the cavity or passage of another part of an animal body. As a rule, or in many instances, the expansible portion of a catheter is a balloon which is introduced into an occlusion in collapsed (non-inflated) condition and is thereupon inflated to thereby open the occlusion. When the inflating step is completed, the balloon is deflated and is ready to be extracted from the opened occlusion and from the animal body.

A drawback of presently known catheters which employ inflatable and deflatable balloons is that a balloon is not likely to invariably open an occlusion or to open an occlusion to a desired extent because its material is too soft and hence too yieldable so that it cannot dislodge a relatively hard region or portion of an occlusion. The only presently known proposal to overcome such problems is to raise the pressure of fluid medium which is used to inflate the balloon. Such solution is not satisfactory because a balloon will expand around a relatively hard region of an occlusion and will not change the position of the hard portion or region at all or only to a negligible extent. Thus, the opened or partly opened occlusion will continue to include one or more hard regions which project well into the body cavity (e.g., into the passage within a blood vessel) with attendant likelihood of renewed occlusion after a relatively short period of time. As a rule, it is desirable that an opened or expanded occlusion exhibit a smooth internal surface.

Therefore, many specialists in the relevant field employ catheters which are actually drilling, milling or boring tools in that their distal ends comprise implements which are designed to remove tissue and/or other material in the region of a stenosis and to thus open the occlusion to the flow of body fluids. Removal of material from a stenosis is often undedesirable and plain dangerous because the removed material migrates in the body cavity and is likely to agglomerate and clog a blood vessel or the like.

U.S. Pat. No. 4,793,359 to Sharrow discloses a transluminal angioplasty catheter wherein the balloon at the distal end of the catheter serves as a means for properly positioning a laser which can direct a hot spot of laser energy onto an occlusion. A drawback of the proposal of Sharrow is that the treatment with laser involves removal of material from an occlusion with the aforediscussed undesirable consequences.

Published European patent application No. 0 246 998 of Porath-Furedi discloses a cardiac balloon catheter which is provided with a bypass conduit to establish a flow path for the blood bypassing the balloon when the balloon is inflated. This publication further discloses a self-supporting split sleeve which is expanded by the balloon and remains implanted in the blood vessel upon completed deflation and removal of the catheter and its balloon. The expanded sleeve has detent means or is otherwise designed to ensure that it remains in the blood vessel, i.e., that it cannot be extracted with the deflated balloon. The purpose of the implanted sleeve is to prevent closing or partial closing of an occlusion. A drawback of such proposal is that a rather large foreign body is left in the blood vessel and is likely to change its position after a certain interval of time, either gradually or abruptly, with attendant danger of clogging and/or injury to the blood vessel.

U.S. Pat. No. 4,796,629 to Grayzel discloses a stiffened dilation balloon catheter wherein certain isolated portions of the inflatable balloon are stiffened to ensure that the balloon can resist deformation of such isolated portions when it is inflated during the treatment procedure. The patented catheter is more likely to dislodge certain hard regions of an occlusion; however, the dislodging action is not reliable because not all portions (the patent refers to isolated reinforced portions) of the balloon are reinforced or stiffened so that hard regions of an occlusion can penetrate between neighboring stiffened portions of the balloon when the latter is expanded within an occlusion. The entire balloon cannot be stiffened because this would prevent its inflation and expansion in response to admission of a supply of pressurized fluid.

Published European patent application No. 0 206 553 of Streatfield et al. discloses an expansible cannula for introduction of instruments, scopes or tubing into a body cavity or organ. The cannula is not designed to open, nor is it capable of opening, an occlusion in a blood vessel or in another body portion or organ. On the contrary, the inventors state that their cannula can be used for placement of catheters into the biliary or urogenital system for drainage.

OBJECTS OF THE INVENTION

An object of the invention is to provide a simple, inexpensive and easy to handle catheter which can be used to open occlusions in blood vessels and for similar purposes.

Another object of the invention is to provide a catheter which can reliably dislodge all parts of an occlusion, even if such parts or some of these parts would be likely to readily resist the dislodging action of an inflatable balloon.

A further object of the invention is to provide a novel and improved distal end for a catheter of the above outlined character.

An additional object of the invention is to provide a catheter which need not remove tissue and/or other materials in the course of opening an occlusion.

Still another object of the invention is to provide a catheter which can reliably open one or more occlusions, either simultaneously or one after the other, in a simple and time saving manner.

A further object of the invention is to provide a catheter which can be withdrawn from an opened occlusion in its entirety to thus avoid long-lasting implantation of foreign bodies in an organ or in another body portion which necessitates treatment.

An additional object of the invention is to provide a novel and improved method of opening occlusions irrespective of the nature and/or composition of occlusions.

Another object of the invention is to provide a catheter which can be designed to readily penetrate into hard-to-reach body cavities and which can be designed to prevent any and all contact between a balloon and an occlusion.

A further object of the invention is to provide a novel and improved method of enhancing the flexibility of the distal end of a catheter.

An additional object of the invention is to provide a catheter which ensures that an opened occlusion presents a smooth surface to the flow of body fluids.

SUMMARY OF THE INVENTION

The invention is embodied in a catheter having a proximal end and a distal end which latter is insertable into a body cavity (e.g., into a blood vessel). The distal end of the catheter comprises an at least partly elastic sleeve which is expansible from a smaller diameter for convenient introduction into an occlusion in a body cavity to a larger diameter to thereby open the occlusion. The sleeve tends to contract to its smaller diameter to thus facilitate extraction from the body cavity upon completed opening of the occlusion, and the sleeve exhibits a stiffness which suffices to resist localized deformation (e.g., the formation of a dent by a relatively hard part of the occlusion) by an occlusion during expansion in the occlusion. The catheter further comprises means for expanding the sleeve upon completed introduction into an occlusion.

In accordance with a presently preferred embodiment, the expanding means comprises an inflatable balloon in the sleeve.

The sleeve can resemble or constitute a scroll (i.e., a preferably metallic or plastic sheet which is rolled into a tube) which comprises an inner marginal portion and an outer marginal portion overlying the inner marginal portion at least in the contracted condition of the sleeve. At least one of the marginal portions moves relative to the other marginal portion in the circumferential direction of the sleeve during expansion and contraction of the sleeve. If the expanding means comprises a balloon which is disposed in or which can be introduced into the sleeve, the inner marginal portion of the scroll can be connected to the balloon. Alternatively, the outer marginal portion of the scroll-shaped sleeve can be connected to an elongated flexible carrier which extends from the proximal end toward the distal end of the catheter. The means for connecting the outer marginal portion of the scroll-shaped sleeve to the carrier can comprise one or more flexible webs.

The dimensions of the scroll-shaped sleeve and the extent of expansion of the sleeve can be selected in such a way that the inner and outer marginal portions barely overlap or are closely adjacent each other and define a narrow clearance in the expanded condition of the sleeve.

The circumferential length of the contracted sleeve can be a fraction of the width (between the two marginal portions) of the sheet or blank which must be convoluted to constitute the scroll-shaped sleeve; for example, the width can be between 125 and 300% of the circumferential length of the contracted sleeve.

The marginal portions of the scroll-shaped sleeve can have a helical shape.

It is also possible to employ a sleeve which constitutes a plastic hose and has at least one substantially longitudinally extending slit or slot which widens in response to expansion of the hose.

At least that portion of the sleeve which is adjacent its external surface can be made of a friction-reducing material.

The sleeve can include a tubular inner section which need not be elastic at all or can be only slightly elastic, and an elastic jacket which surrounds the inner section and tends to contract to thereby reduce the diameter of the inner section except when the expanding means is operative to increase the diameter of the sleeve by expanding the inner section from within. The jacket can contain latex.

The sleeve can be provided with one or more circumferentially extending weakened portions (such as arcuate slits) to facilitate flexing of the sleeve, e.g., during penetration into a blood vessel).

It is also possible to assemble the sleeve from a plurality of relatively short tubular sections or portions which are connected to each other end-to-end and render the sleeve flexible. At least two tubular sections or portions can constitute scrolls with inner and outer marginal portions. The arrangement is preferably such that the marginal portions of one scroll are angularly offset relative to the marginal portions of the other scroll.

The expanding means can comprise one or more basket-shaped or otherwise configurated mechanical springs. Each spring is movable relative to the sleeve (and/or vice versa) in the axial direction of the sleeve so that the spring can penetrate into and then expand the sleeve or is extracted from the sleeve to thus enable the sleeve to contract.

The novel features which are considered as characteristic of the invention are set forth in particular in the appended claims. The improved catheter itself, however, both as to its construction and the mode of assembling and using the same, together with additional features and advantages thereof, will be best understood upon perusal of the following detailed description of certain presently preferred specific embodiments with reference to the accompanying drawing.

DESCRIPTION OF PREFERRED EMBODIMENTS

Figure 1:
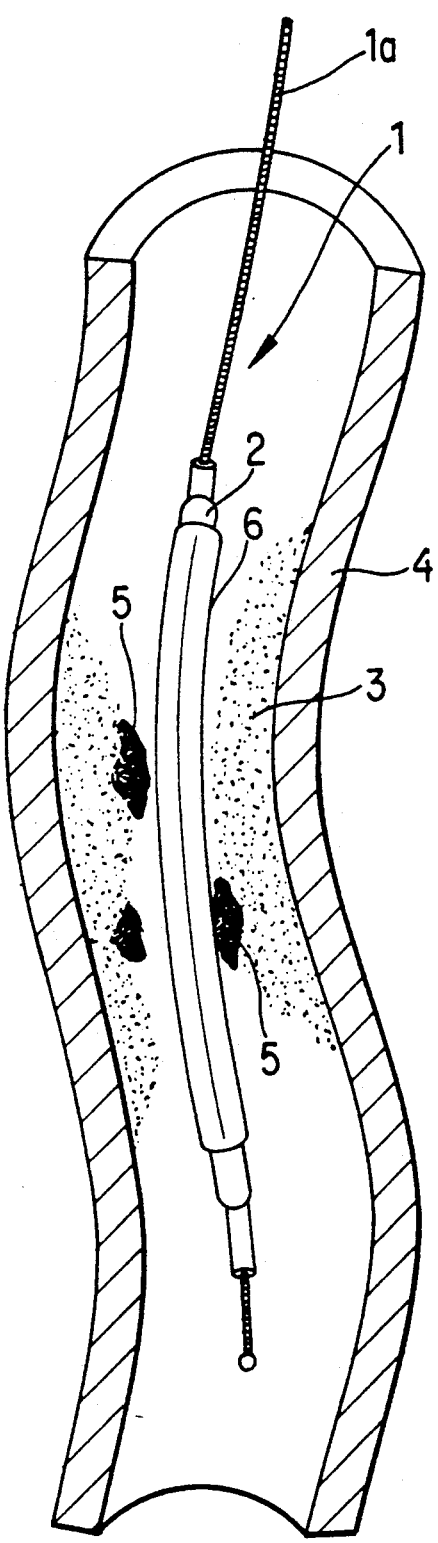
FIG. 1 is a greatly enlarged fragmentary longitudinal sectional view of a blood vessel with an occlusion, and a perspective view of a portion of a catheter which embodies one form of the invention, the distal end of the catheter being surrounded by the occlusion.
Figure 2:
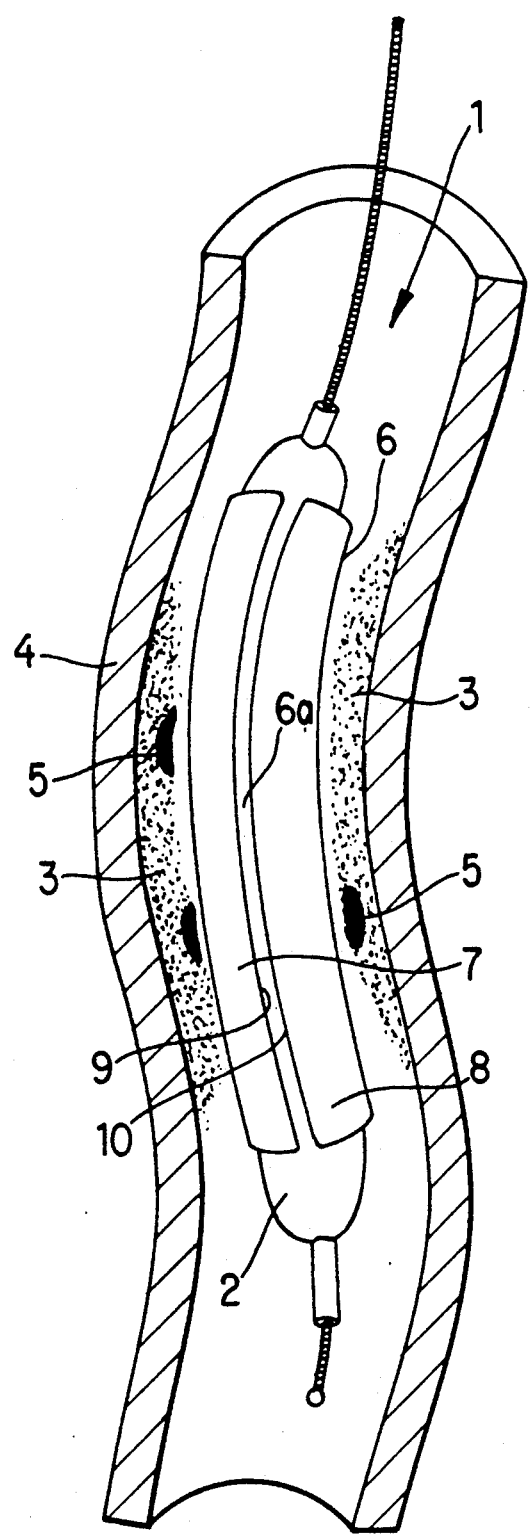
FIG. 2 shows the structure of FIG. 1 but with the sleeve at the distal end in expanded condition in which the occlusion is opened.

FIGS. 1 and 2 show a portion of a body cavity which is constituted by the passage of a blood vessel 4. The cavity contains an occlusion in the form of a stenosis 3 including relatively hard regions or portions denoted by the character 5. The occlusion 3 is to be opened or enlarged by the distal end of a novel and improved catheter 1 including an elongated flexible tubular carrier 1a extending from the proximal end (not shown) toward the distal end and supporting a novel and improved elongated tubular sleeve 6 which is disposed at the distal end and surrounds a balloon 2 serving as a means for expanding the sleeve from a smaller diameter (shown in FIG. 1) to a larger diameter (shown in FIG. 2) in response to admission of a pressurized fluid through the carrier 1a.

As can be seen in FIG. 1, the relatively hard regions 5 of the occlusion 3 extend well toward the center of the passage in the blood vessel 4 and are thus first to be contacted by the sleeve 6 when the latter is expanded as a result of admission of a pressurized fluid into the balloon 2. In order to avoid localized deformation of the sleeve 6 (i.e., the formation of smaller or larger dents as a result of impact against the hard regions or portions 5 of the occlusion 3), the sleeve 6 is at least slightly elastic but is sufficiently stiff to prevent localized deformation when its diameter increases from that which is shown in FIG. 1 to that which is shown in FIG. 2. The sleeve 6 is preferably made of a suitable metallic or plastic material. The selected material is preferably such that the sleeve 6 is relatively hard, i.e., it is capable of increasing its diameter by having its normally overlapping marginal portions 7 and 8 (see FIGS. 3, 5 and 7) slide relative to each other to positions in which they barely overlap or are rather closely adjacent to each other (see FIGS. 2 and 7) so that the edges 9, 10 of their marginal portions 7, 8 define a rather narrow clearance or gap 6a. The width of such clearance is insufficient to enable a hard region 5 to contact the relatively soft balloon 2 so that such hard region is not displaced radially outwardly toward the internal surface of the blood vessel 4. When the sleeve 6 is free to contract (the sleeve exhibits a tendency to contract and to assume the condition which is shown in FIG. 1), it completely surrounds the balloon 2 so that the latter is shielded during introduction of the distal end of the catheter 1 into the occlusion 3. The sleeve 6 is thereupon expanded in response to inflation of the balloon 2 to thereby open the occlusion 3 and to push the hard regions 5 further away from the passage in the blood vessel 4 (see FIG. 2). Such radially outward displacement of the entire occlusion 3 (including its hard regions 5) is effected without removal of any tissue or any parts of the occlusion but solely as a result of pressure which is generated by the expandible sleeve 6 in response to inflation of the balloon 2 by a pressurized fluid which is supplied through the carrier 1a of the catheter 1.

Figure 3:
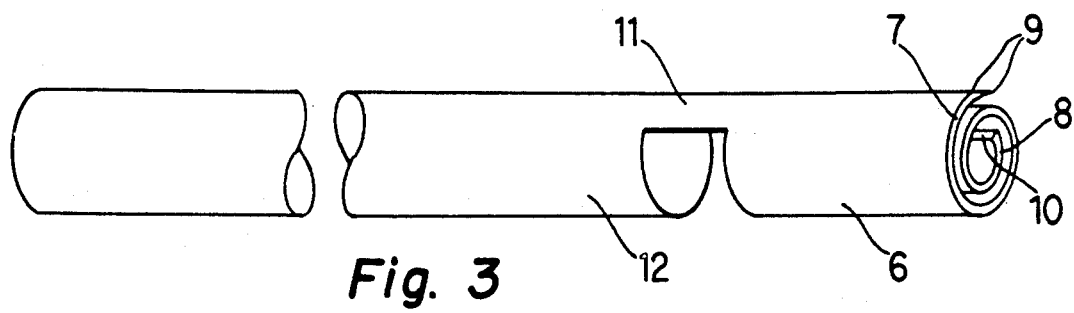
FIG. 3 is an enlarged perspective view of the sleeve at the distal end of the catheter of FIG. 1 in contracted condition, and further showing a portion of a carrier for the sleeve.
Figure 4:
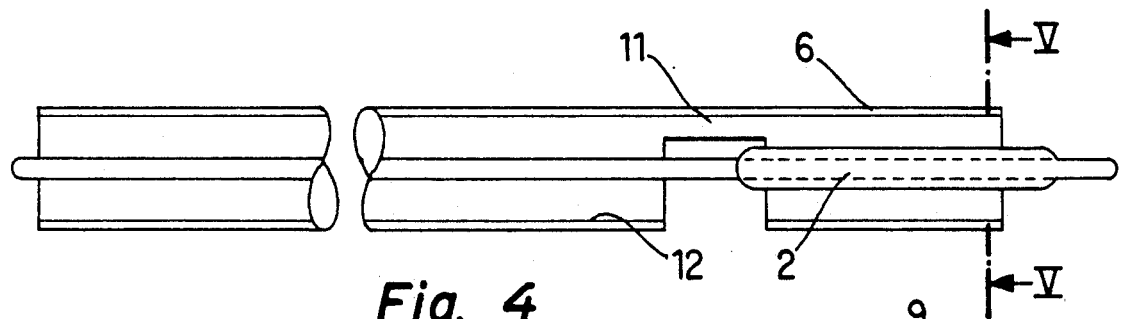
FIG. 4 is a central longitudinal sectional view of the sleeve and of its carrier, and further showing the balloon in non-inflated condition as well as a conduit for admission of a pressurized fluid into the balloon.
Figure 5:
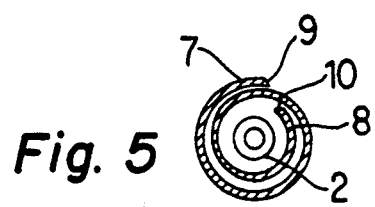
FIG. 5 is a transverse sectional view as seen in the direction of arrows from the line V—V of FIG. 4.
Figure 6:
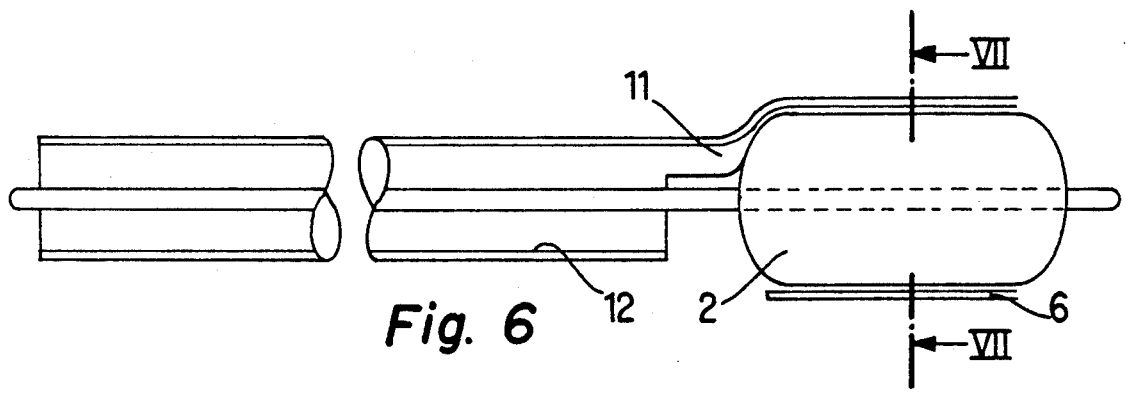
FIG. 6 shows the structure of FIG. 4 but with the balloon inflated and the sleeve in expanded condition.
Figure 7:
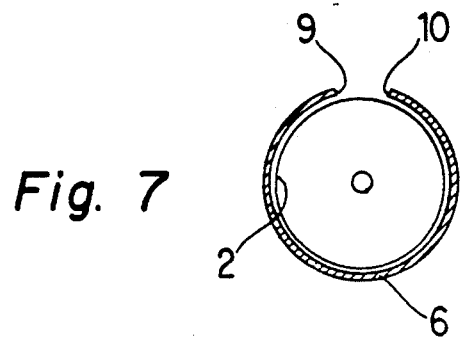
FIG. 7 is a sectional view as seen in the direction of arrows from the line VII—VII in FIG. 6.

FIGS. 3, 5 and 7 show that the sleeve 2 constitutes a scroll, i.e., it is made of a sheet or panel of metallic or plastic material which is rolled up so that the outer marginal portion 7 overlies (i.e., is located radially outwardly of) the inner marginal portion 7. When the balloon 2 is inflated to assume the shape which is shown in FIGS. 6 and 7, the marginal portion 7 slides circumferentially of the sleeve 6 relative to the marginal portion 8 and/or vice versa. As can be seen in FIG. 5, the deflated or non-inflated balloon 2 is surrounded by at least two layers or convolutions of the coiled sheet material of the sleeve 6, and the diameter of the sleeve 6 can be increased by 100% or more in response to inflation of the balloon upon completed introduction of the distal end of the catheter 1 into an occlusion 3 which is to be treated. The width of the clearance 6a between the edges 9, 10 of marginal portions 7, 8 of the expanded sleeve 6 which is shown in FIG. 7 is exaggerated for the sake of clarity. In fact, at least in many or most instances, the dimensions of the sleeve 6 and the extent of inflation of the balloon 2 will be selected in such a way that the marginal portion 7 continues to overlap (e.g., barely overlap) the marginal portion 8 when the sleeve 6 is fully expanded in a body cavity.

The designer of the improved catheter 1 knows the desired maximum diameter of the sleeve 6 (in fully inflated condition of the balloon 2) so that such designer can readily calculate the dimensions of the blank which is to be converted into the sleeve 6 in such a way that the marginal portions 7, 8 will continue to overlap in the fully expanded condition of the sleeve or that the edges 9, 10 of the marginal portions 7, 8 will define a very narrow clearance 6a which does not permit a hard region 5 of the occlusion 3 to remain at the original distance from the internal surface of the blood vessel 4 in response to inflation of the balloon. Moreover, and in order to even more reliably ensure that each and every hard region 5 of an occlusion 3 which is to be opened will be displaced radially outwardly toward the internal surface of the blood vessel 4, the person in charge of manipulating the catheter 1 can deflate the inflated balloon 2 at least once prior to changing the angular position of the sleeve 6 (which contracts in automatic response to deflation of the balloon) so that a different portion of the external surface of the turned or reoriented sleeve 6 will be adjacent each of the hard regions 5 with the result that renewed inflation of the balloon will invariably ensure adequate opening of the occlusion and radially outward displacement of each and every hard region 5. Such precautionary measures (repeated inflation and deflation of the balloon 2 and turning of the sleeve 6 in ah occlusion 3) are actually necessary only and alone when the expansion of the sleeve is as pronounced as shown in FIGS. 2 and 7, i.e., that the marginal portions 7, 8 of the sleeve no longer overlap.

The catheter 1 is preferably provided with means for connecting the sleeve 6 with the carrier 1a and/or with the balloon 2. This ensures that the sleeve 6 follows all axial movements of the carrier 1a (i.e. that it can be introduced into or withdrawn from an occlusion in a body cavity in response to appropriate manipulation of the proximal end of the carrier) as well as that the sleeve can be turned in an occlusion at least subsequent to deflation of the balloon 2. For example, the connecting means may include a suitable adhesive which bonds the outer marginal portion 7 to an elongated flexible tube 12 of the carrier 1a or which bonds the inner marginal portion 8 directly to the balloon 2. FIGS. 3 to 6 show that embodiment wherein the flexible tube 12 is connected to the adjacent proximal end of the marginal portion 7 by a flexible web 11 which is integral with the parts 6 and 12. If the illustrated flexible tube 12 is replaced with a tube having a smaller diameter (e.g., a diameter matching or approximating that of the deflated or non-inflated balloon 2 in FIG. 4), the distal end of such smaller-diameter tube 12 can be bonded to or made of one piece with the inner marginal portion 8 of the sleeve 6.

The sleeve 6 (or at least that portion of the sleeve which is adjacent its external surface) is preferably made of a friction-reducing material, particularly a plastic sheet material or a metallic sheet material which enables the marginal portions 7, 8 to readily slide along the adjacent portions of the internal and external surfaces of the sleeve 6 when the latter expands to increase its diameter as a result of inflation of the balloon 2 or when the sleeve contracts in automatic response to deflation of the balloon. The material of the sleeve 6 which is shown in FIGS. 1 to 7 is sufficiently elastic to ensure that the sleeve will invariably seek to contract (to a diameter which is shown in FIGS. 1, 3 and 5) as soon as it is permitted to do so in view of the condition of the balloon 2.

The extent of overlap of marginal portions 7, 8 of the scroll-shaped sleeve 6 depends on the desired maximum diameter of the balloon 2 in response to inflation as a result of admission of pressurized fluid via carrier 1a. For example, the width of the blank which is converted into the scroll-shaped sleeve 6 (as measured between the edges 9, 10 of the marginal portions 7, 8) can exceed the circumferential length of the contracted sleeve by at least 100%, preferably more than 100%. In FIG. 5, the width is approximately twice the circumferential length of the contracted sleeve 6, i.e., the entire balloon 2 is surrounded by two layers or convolutions of the sheet material of the scroll-like sleeve 6. It is normally preferred to select the aforementioned width to circumferential length ratio in such a way that the width exceeds the circumferential length of the contracted sleeve by 125-300%.

In FIG. 5, the external surface of the non-inflated balloon 2 is spaced apart from the inner marginal portion 8 of the contracted sleeve 6. This is shown solely for the sake of clarity because, in actual practice, the inner marginal portion 8 is immediately adjacent and is or can be bonded to the external surface of the non-inflated balloon 2. This ensures that the sleeve 6 begins to expand in immediate response to admission of pressurized fluid into the non-inflated balloon 2, i.e., that each and every stage of the operation of increasing the diameter of the originally deflated or non-inflated balloon entails an increase of the outer diameter of the sleeve 6. This holds true even though the material of the sleeve 6 is relatively stiff (to avoid localized deformation, such as denting by one or more hardened regions 5 of an occlusion 3).

When the sleeve 6 is properly introduced into the occlusion 3 so that its external surface is adjacent all of the illustrated hard regions 5, the carrier 1a is caused to admit a compressed fluid which inflates the balloon 2 to thereby increase the outer diameter of the sleeve 6. The external surface of the expanding sleeve then pushes all hard regions 5 as well as all other radially inner portions of the occlusion 3 radially outwardly toward the internal surface of the blood vessel 4 to the same extent (FIG. 2) so that the entire occlusion is opened to the same extent to provide a relatively large path for the flow of a body fluid as soon as the balloon 2 is deflated (i.e., as soon as the sleeve 6 is permitted to contract to reassume the condition which is shown in FIG. 1), whereupon the entire catheter 1 including the sleeve 6 is withdrawn from the body cavity. Opening of the occlusion 3 takes place without any material removal by the expanding or contracting sleeve 6 which is desirable and advantageous because the removed tissue and/or other material could clog the blood vessel, i.e., by gathering in another occlusion. Moreover, the sleeve 6 can be readily turned in the vessel 4 because such turning does not and need not involve removal of any tissue or other material which could result in damage to the blood vessel.

The improved catheter 1 exhibits all advantages of conventional balloon catheters but does not embody the drawbacks of such presently used instruments. The reason is that the material which forms an occlusion is not permitted, or need not be permitted, to actually contact the balloon 2 which is desirable and advantageous because the yieldability of a balloon (in response to inflation against one or more relatively hard portions or regions of an occlusion) is much more pronounced than that of the improved sleeve 6. Therefore, the opening of an occlusion by utilizing the improved catheter 1 is much more predictable than a treatment of occlusions with conventional instruments that employ balloons.

An important advantage of the improved catheter 1 is that the sleeve 6 invariably tends to contract so that it is ready to be withdrawn from a body cavity as soon as the treatment of an occlusion is completed, i.e., as soon as the balloon 2 is deflated and/or the spring or springs which are used in lieu of or jointly with the balloon have their diameters reduced for convenient extraction of the distal end of the catheter by the same route as during introduction of the sleeve into an occlusion. Moreover, the improved catheter need not remove any tissue and/or other material during insertion into or during extraction from a body cavity and/or during opening of an occlusion. All that is necessary is to employ a sleeve which exhibits the required tendency to contract and can be connected to a carrier for introduction into and for withdrawal from a body cavity, and to provide suitable means (one or more balloons and/or one or more springs) for controlled expansion of the sleeve within an occlusion.

Experiments with the improved catheter indicate that the sleeve 6 is capable of predictably and optimally opening an occlusion even if the latter comprises one or more hard or very hard regions which would invariably depress the adjacent portion of a balloon if they were to be directly engaged by an expanding balloon. Moreover, the sleeve 6 ensures highly desirable smoothing of the internal surface of an opened occlusion so that the opened occlusion is much less likely to intercept and accumulate particles which float in the body fluid. In addition, the improved catheter need not and does not remove material from the blood vessel or another part of the body, either during introduction of the distal end of the catheter into an occlusion, during opening of the occlusion and/or during extraction of the distal end (subsequent to contraction of the sleeve). The material and the thickness of the sleeve can be readily selected in such a way that the sleeve can reliably dislodge very hard regions of an occlusion to thus ensure the establishment of a path which is surrounded by a smooth surface (within the opened occlusion) to avoid interception of floating particles and to permit convenient extraction of the distal end as soon as the sleeve is permitted to reassume its contracted condition.

The feature that the sleeve 6 constitutes or resembles a scroll is desirable and advantageous because this enables the sleeve to expand in a highly predictable manner as well as to contract upon completed opening of one or more occlusions preparatory to withdrawal from the expanded or opened occlusion or occlusions and from the body of a patient. The expanding or opening operation is even more reliable if the inner marginal portion 8 of a scroll-shaped sleeve 6 is connected to the balloon or if the outer marginal portion 7 is connected to the carrier. This ensures highly predictable expansion and contraction of the sleeve. The connection between a marginal portion of the sleeve and the balloon or the carrier can be obtained by resorting to a suitable adhesive, by welding or in any other suitable way. Furthermore, the designer of the improved catheter can ensure that the entire balloon is always surrounded by at least one circumferentially complete cylindrical wall of the sleeve, even when the balloon is fully inflated, as long as the marginal portions 7, 8 of the scroll-shaped sleeve continue to overlap each other, also in the fully inflated condition of the balloon. This reduces the likelihood of damage to the balloon and ensures predictable opening of an entire occlusion irrespective of the number and distribution of hard regions 5.

By making the entire sleeve, or at least a portion of the sleeve, from a material which has a low coefficient of friction, one ensures that the sleeve will more readily and more predictably expand or contract in response to inflation or deflation of the balloon. Moreover, the utilization of such material is desirable and advantageous for convenience of introduction of the distal end of the catheter into or its extraction from an occlusion. There are many types of metallic and plastic materials which exhibit desirable friction-reducing characteristics and can be utilized for the making of a portion of or the entire sleeve 6.

Figure 8:
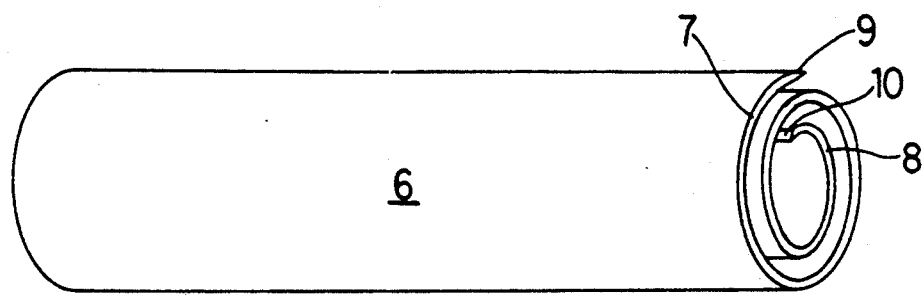
FIG. 8 is a greatly enlarged perspective view of the sleeve which is shown in unexpanded condition.

FIG. 8 shows a scroll-shaped sleeve 6 which is similar to the sleeve of FIGS. 1 to 7. The balloon 2 is omitted and the sleeve 6 is shown in contracted condition in which it forms two complete convolutions so that, when it surrounds a non-inflated balloon, each and every portion of the external surface of the balloon is surrounded by two layers of material of the contracted sleeve.

Figure 9:
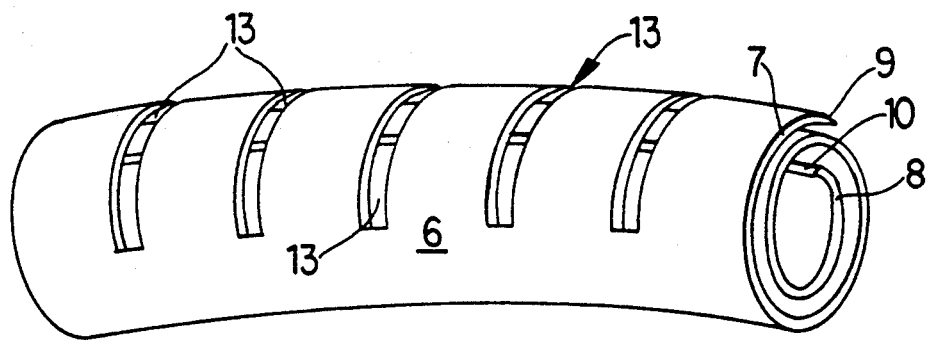
FIG. 9 is a similar perspective view of a modified sleeve which can be flexed for convenient introduction into and withdrawal from a body cavity.

FIG. 9 shows that the sleeve 6 is provided with several circumferentially extending weakened portions in the form of notches or slots 13 which enhance the flexibility of the sleeve so that the latter can be more readily introduced into a selected portion of a body cavity, e.g., into an occlusion 3 of the type shown in FIG. 1. The weakened portions 13 can include slots which extend all the way from the internal surface to the external surface of the sleeve 6, or they may include thinner portions of the sleeve. The illustrated weakened portions 13 extend from the edge 9 of the marginal portion 7 toward but short of the marginal portion 8 and its edge 10. It is possible to provide one or more substantially circumferentially extending weakened portions which begin at the edge 10 of the inner marginal portion 8 and extend toward but short of the outer marginal portion 7. This would even further enhance the flexibility of the sleeve 6 for the purposes of convenient and rapid introduction into a selected portion of a body cavity. Each weakened portion 13 can consist of a row of shorter weakened portions, e.g., of a row of slots each of which extends all the way between the internal and external surfaces of the sleeve 6. The enhanced flexibility of the sleeve 6 of FIG. 9 in view of the provision of several arcuate weakened portions 13 is indicated by the curvature of this sleeve (compare with the substantially straight sleeve 6 of FIG. 8). At least a certain amount of flexibility of the sleeve 6 is desirable on the aforementioned ground that such sleeve can be more readily introduced into a selected portion of a body cavity, even along a tortuous path. Reference may be had to the commonly owned copending patent application Ser. No. 07/585,293 filed Sep. 19, 1990 for "Guide for introduction of catheters into blood vessels and the like". An additional ground for the utilization of a flexible sleeve 6 is that such sleeve can be made longer than a sleeve which offers a more pronounced resistance to flexing since it can be more readily advanced along a sinuous or other complex path, for example, into a relatively small blood vessel which branches off a larger vessel which, in turn, branches off a still larger vessel. A relatively long sleeve 6 can be used to open a relatively long occlusion 3 or to simultaneously open two or more occlusions which are adjacent each other.

Figure 10:
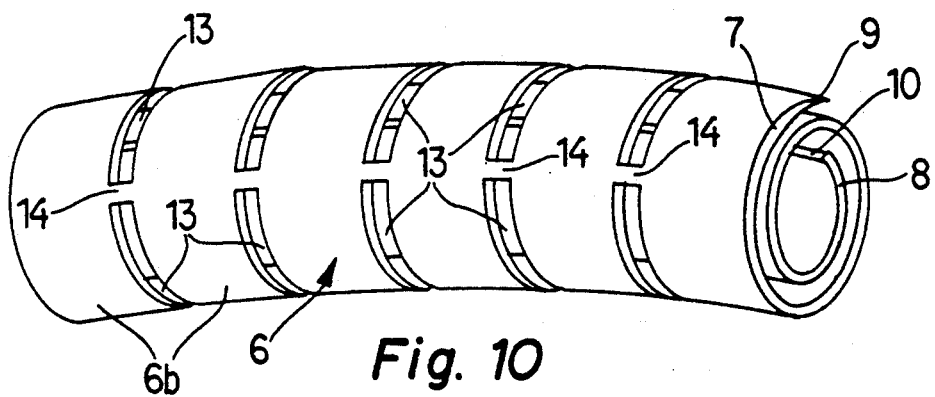
FIG. 10 is a perspective view of a sleeve which constitutes a first modification of the sleeve of FIG. 9.

FIG. 10 shows a sleeve 6 which constitutes a modification of the sleeve 6 of FIG. 9. The sleeve 6 of FIG. 10 includes a plurality of relatively short tubular portions or sections 6b which are disposed end-to-end and each of which resembles a relatively short scroll. The neighboring tubular portions or sections 6b are connected to each other by narrow webs 14 to bridge the circumferentially extending notches or slots 13 between neighboring tubular portions. The flexibility of the sleeve 6 of FIG. 10 is even more pronounced than that of the sleeve which is shown in FIG. 9. The sleeve 6 of FIG. 10 is obtained by cutting windows into a blank which is then rolled up to form a scroll-like sleeve, i.e., the webs 14 are integral parts of and are of one piece with neighboring tubular portions 6a of the sleeve of FIG. 10. However, it is equally possible to assemble the sleeve 6 of FIG. 10 from a selected number of separately produced tubular portions or sections which are bonded or otherwise connected to each other, e.g., at locations corresponding to those of the webs 14 which are shown in FIG. 10, to produce a readily flexible sleeve which can be expanded by a balloon (not shown in FIG. 10) or in any other suitable way.

Figure 11:
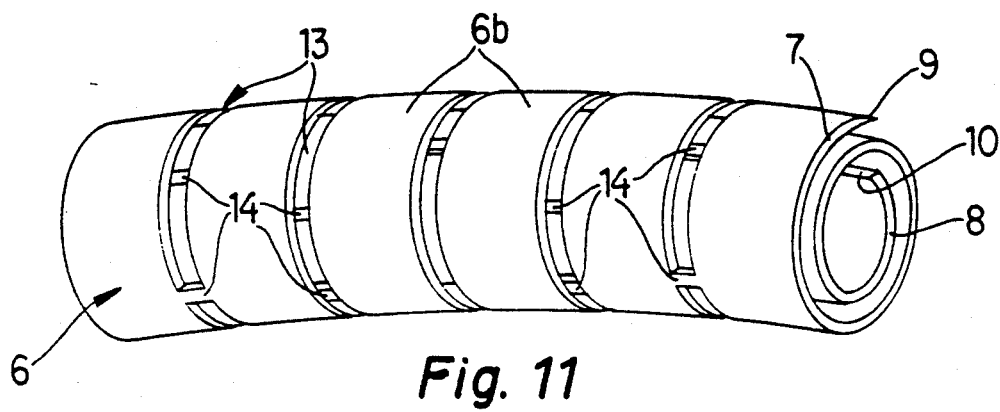
FIG. 11 is a perspective view of a sleeve which constitutes a second modification of the sleeve of FIG. 10.

FIG. 11 shows a sleeve 6 which is modified version of the sleeve of FIG. 9. The difference is that the weakened portions 13 of the sleeve 6 of FIG. 11 are longer than the weakened portions 13 of FIG. 9. The webs 14 between the neighboring tubular sections or portions 6a of the sleeve 6 of FIG. 1 are or can be staggered relative to each other in the circumferential direction of the sleeve from weakened portion 13 to weakened portion 13. This, too, enhances the flexibility of the finished sleeve.

The weakened portions 13 will not extend all the way between the internal and external surfaces of the respective sleeve 6 if it is desired to avoid direct contact between a balloon 2 and the occlusion 3 in a body cavity. Thus, each such weakened portion can include a groove or recess in the internal and/or external surface of the respective sleeve 6 so that the material at the bottom of such recess or groove overlies the adjacent portion of the balloon and shields the relatively soft and more readily deformable balloon from undesirable deformation by one or more hardened regions 5 of an occlusion 3. The weakened portions 13 which do not include slots extending all the way between the internal and external surfaces still suffice to at least slightly enhance the flexibility of the sleeve in order to permit the utilization of a longer sleeve and/or more convenient steering of the sleeve on its way into a selected portion of a body cavity. Moreover, a sleeve which is not provided with weakened portions in the form of slots is less likely to remove tissue on its way into or out of a body cavity because the edges bounding the recesses or grooves are not as pronounced and as sharp as those bounding slots which extend all the way through the corresponding portions of a sleeve.

An advantage of the sleeves which are shown in FIGS. 9 to 11 is that these sleeves exhibit a pronounced flexibility without affecting their basic purpose of ensuring predictable opening of occlusions irrespective of whether or not an occlusion includes one or more hard regions 5. Flexibility of the sleeve 6 is desirable and advantageous because this greatly simplifies the introduction of the distal end of the catheter into and its withdrawal from a selected portion of a body cavity. Moreover, it is even possible to employ one and the same flexible sleeve to simultaneously open two neighboring occlusions which are disposed at a certain angle to each other. The sleeves 6 of FIGS. 9 to 11 can be weakened prior to rolling the respective blanks into scroll-shaped bodies. However, and as already pointed out hereinabove, it is possible to assemble a sleeve from several separately produced tubular portions or sections which are thereupon welded, glued or otherwise connected to each other with freedom of tilting movement to thus ensure desirable flexibility of the completed sleeve.

Flexibility of a sleeve 6 renders it possible to employ a relatively long balloon and an equally long sleeve even if the distal end embodying a long balloon and a long sleeve is to be introduced along a complex path which includes one or more arcuate portions Alternatively or in addition to this feature, a distal end with a relatively long balloon and a relatively long sleeve can be used for simultaneous opening of two or more neighboring occlusions. In fact, a distal end employing a relatively long but readily flexible sleeve can be used to open up one or more occlusions while being located in an arcuate body cavity, e.g., in a vessel having a pronounced bend with an occlusion in each of the two mutually inclined portions of the bend.

The sleeve 6 of FIG. 11 exhibits the additional advantage that, due to circumferential staggering of the webs 14 in some or all of the weakened portions 13, the areas of frictional engagement between neighboring walls of the scroll-shaped sleeve 6 are staggered in the circumferential direction of the sleeve which is desirable and advantageous during contraction as well as during expansion of such sleeve. Distribution of locations of frictional engagement between neighboring convolutions of the sleeve 6 is of advantage in each of these instances, not only because the wear upon the sleeve is more uniformly distributed in the axial and circumferential directions but also because this enhances the flexibility of the sleeve and ensures that a lesser force is necessary to flex the sleeve during introduction into or during withdrawal from a body cavity.

Figure 12:
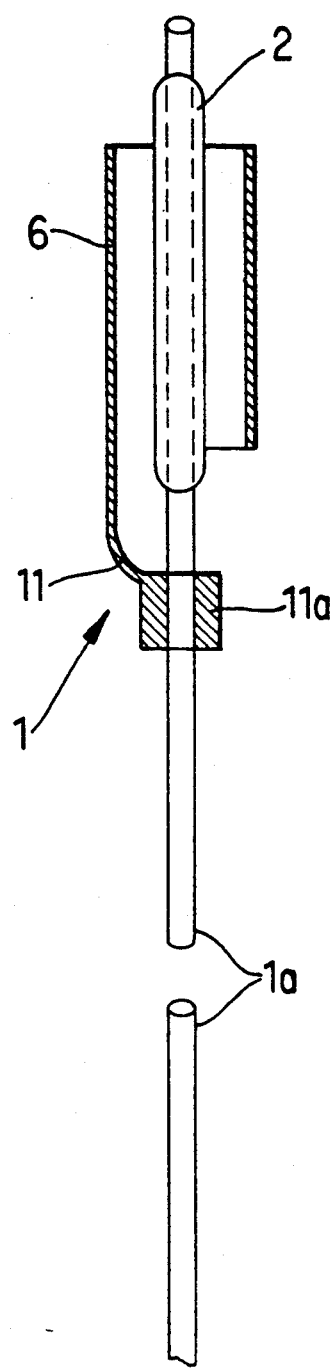
FIG. 12 is an enlarged partly elevational and partly central sectional view of a catheter wherein the sleeve is connected to its carrier by a collar.
Figure 13:
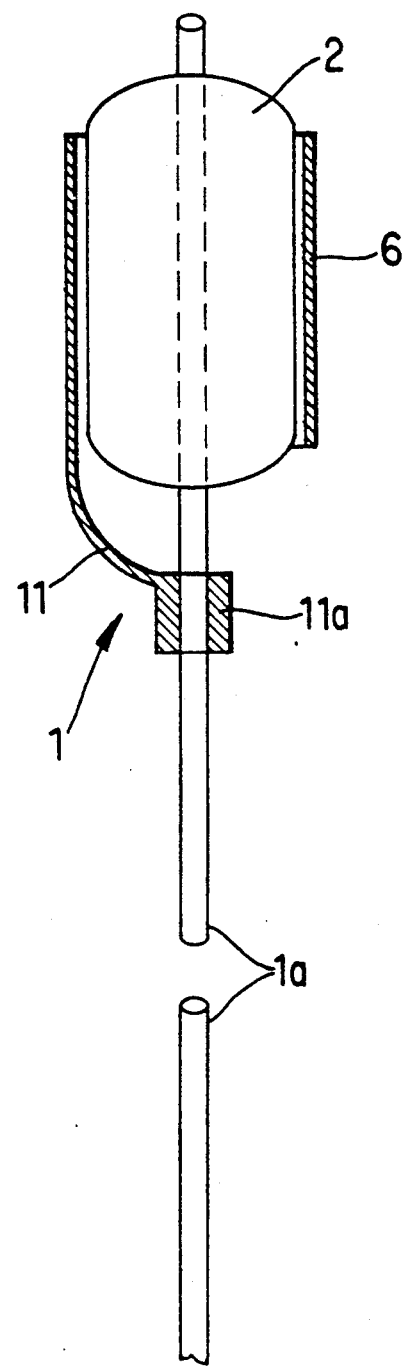
FIG. 13 shows the structure of FIG. 12 in expanded condition of the sleeve.

FIGS. 12 and 13 show a different catheter 1 wherein the sleeve 6 is integral with a web 11 provided with a collar 11a which surrounds the carrier 1a. When the balloon 2 is inflated, the outer diameter of the radially expansible sleeve 6 increases from that which is shown in FIG. 12 to that which is shown in FIG. 13. As shown, the distal end of the balloon 2 can extend beyond the distal end of the sleeve 6.

Figure 15:
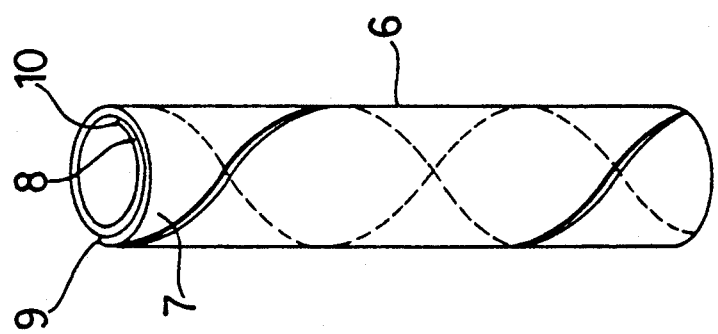
FIG. 15 shows the sleeve of FIG. 14 in contracted condition.
Figure 14:
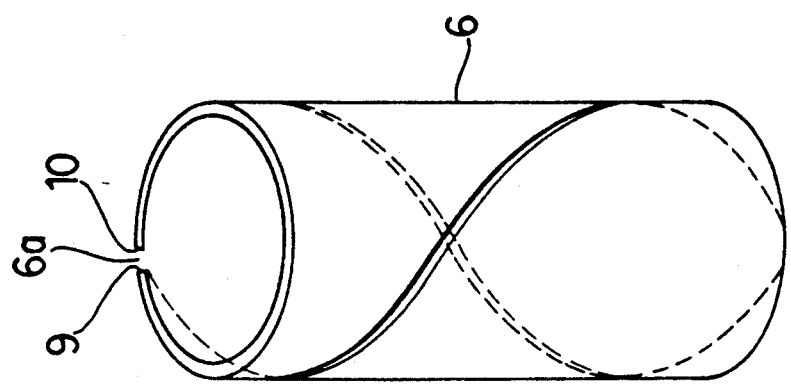
FIG. 14 is a perspective view of a scroll-like sleeve with helical marginal portions, the sleeve being shown in the expanded condition.

FIGS. 14 and 15 show a scroll-shaped sleeve 6 with helical marginal portions 7 and 8 having edges 9 and 10, respectively. The helical marginal portions contribute to flexibility of the sleeve 6 which is important when the sleeve is permitted to contract (FIG. 15) to be introduced into a body cavity and into a selected occlusion in such body cavity. FIG. 14 shows the sleeve 6 in expanded condition in which the edges 9, 10 of the marginal portions 7, 8 define a very narrow helical clearance or gap 6a. Such clearance will develop only in the fully expanded condition of the sleeve 6 and is not likely to develop under most circumstances of actual use of a catheter the distal end of which includes a sleeve of the type shown in FIGS. 14 and 15.

The sleeve 6 of FIGS. 14 and 15 can be said to embody the features of the sleeves which are shown in FIGS. 9 to 11 because each of the helical marginal portions 7, 8 includes weakened parts (valleys) and reinforced parts (hills) so that the flexibility of the sleeve of FIGS. 14, 15 is somewhat more pronounced than that of the sleeve 6 of FIG. 8 wherein the edges 9, 10 of the marginal portions 7, 8 are parallel or nearly parallel to each other. The helical marginal portions 7 and 8 further contribute to more satisfactory distribution of areas of frictional engagement between neighboring convolutions of the sleeve 6.

Figure 16:
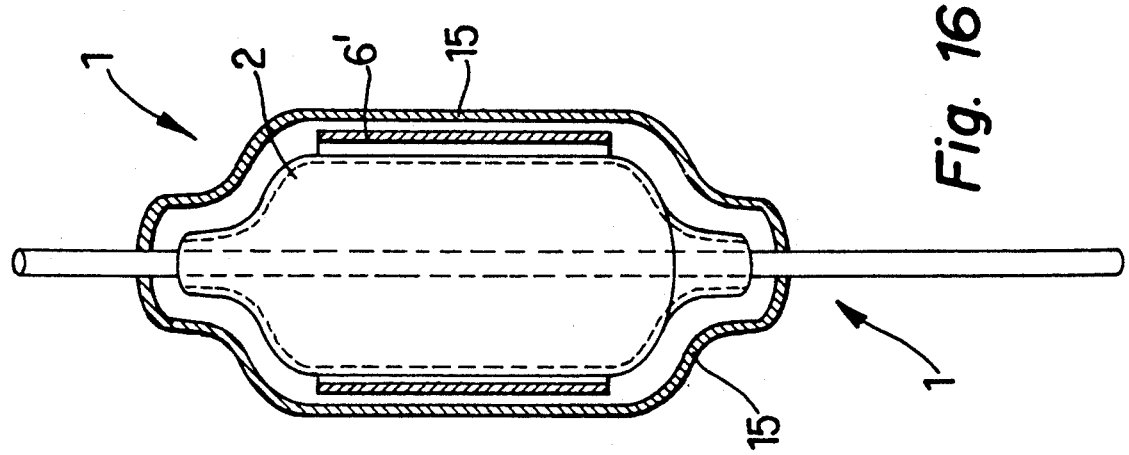
FIG. 16 is a greatly enlarged fragmentary partly elevational and partly longitudinal sectional view of a catheter wherein the sleeve comprises two separately produced parts including a non-elastic or slightly elastic inner section and an elastic jacket which surrounds the inner section.

FIG. 16 shows a catheter 1 wherein the sleeve comprises two sections, namely an expansible inner section 6' and an elastic outer section or jacket 15 which surrounds the inner section 6' and tends to reduce its diameter substantially to that shown in FIG. 1 for the sleeve 6. The jacket 15 is made of a relatively thin elastomeric material (e.g., a material which contains latex), and the tendency of the jacket 15 to reduce its diameter is sufficiently pronounced to ensure that the diameter of the inner section 6' is reduced in automatic response to deflation of the balloon 2.

The jacket 15 can be used in each of the aforedescribed embodiments of the improved catheter. This renders it possible to make the sleeve 6 or the inner section 6' from a material which need not be elastic or which need not exhibit a pronounced elasticity because the jacket 15 ensures immediate contraction of the sleeve 6 or of the inner section 6' as soon as the balloon 2 is free to reduce its outer diameter.

The jacket 15 exhibits the additional advantage that it can fully conceal and shield those (end) portions of the balloon 2 which project beyond the distal and proximal ends of the inner section 6'. It is to be noted that, though FIG. 16 shows a clearance between the inflated balloon 2 and the inner section 6' as well as a clearance between the inner section 6' and the jacket 15, this is merely for clarity of illustration because, in actual use of the improved catheter 1, the expanded balloon bears directly against the internal surface of the radially expanded inner section and the external surface of the expanded inner section bears directly against the internal surface of the elastic jacket. The fact that the material of the jacket 15 is or can be soft does not affect the quality of the opening operation upon an occlusion because the jacket is backed by the relatively stiff inner section 6' which is not likely to develop dents at locations where the external surface of the expanded jacket 15 contacts one or more hard regions 5 of an occlusion 3.

The jacket 15 can be applied over an elastic inner section 6' of the type identical with the section 6 which is described with reference to FIGS. 1 to 15. The pronounced elasticity of the jacket 15 and its tendency to contract even further ensure that the elastic inner section 6' invariably contracts as soon as permitted to do so by the balloon 2.

An additional advantage of the jacket 15 is that it enhances the smoothness of the distal end of the catheter 1. Thus, this jacket overlies the edges at the proximal and distal ends of the inner section 6' as well as the edges 9, 10 (not shown in FIG. 16) which bound the overlapping marginal portions of the scroll-shaped inner section 6'. Such softness of the external surface of the distal end which includes the structure of FIG. 16 facilitates insertion of the catheter 1 into and its extraction from a body cavity. The jacket 15 is particularly desirable and advantageous if the inner section 6' is designed or dimensioned to expand to an extent as shown for the sleeve 6 of FIGS. 2 and 7, i.e., when the marginal portions do not actually overlie each other in the expanded condition of the inner section 6'. The jacket 15 then overlies the clearance 6a to thus prevent pinching of some tissue or of the material of the occlusion 3 between the edges 9, 10 of the marginal portions 7 and 8.

Figure 17:
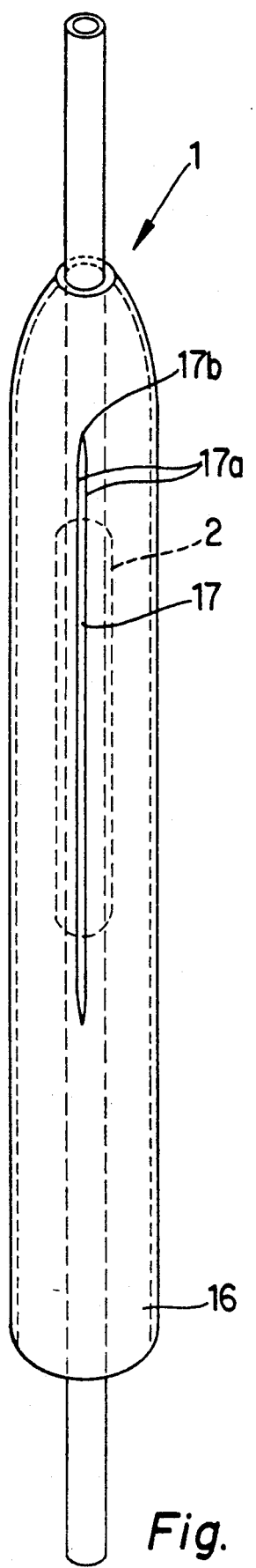
FIG. 17 is an enlarged fragmentary perspective view of a catheter wherein the sleeve is constituted by an elongated hose with one or more longitudinally extending slits which are closed in non-inflated condition of the balloon.
Figure 18:
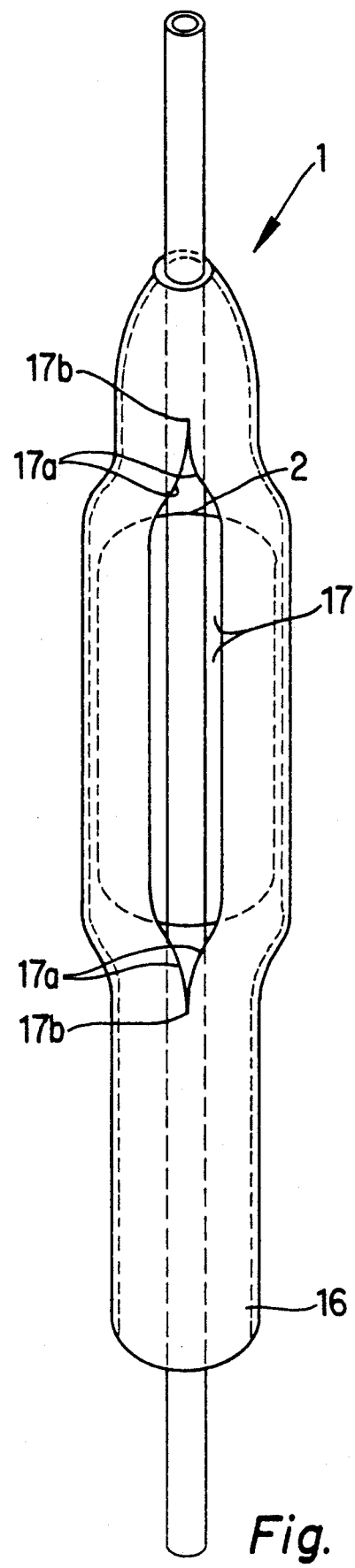
FIG. 18 illustrates the structure of FIG. 17 but with the hose in expanded condition.

FIGS. 17 and 18 show a portion of a further catheter 1 wherein the sleeve does not resemble or constitute a scroll but rather an elongated hose 16 which surrounds the balloon 2 and extends well beyond the proximal and distal ends of the balloon. The sleeve or hose 16 is preferably made of a suitable plastic material. This sleeve is an elongated cylinder which has a substantially constant diameter from end to end (see FIG. 17) when the balloon 2 is not inflated. The means for permitting radial expansion of the sleeve or hose 16 in response to inflation of the balloon 2 (see FIG. 18) includes one or more elongated slits 17 which are provided in the median portion of the sleeve and can extend beyond the distal and proximal ends of the balloon. When the balloon 2 is inflated, the width of the slit or slits 17 increases to thus permit an increase of the outer diameter of the hose or sleeve 16 with attendant opening of an occlusion (not shown in FIGS. 17 and 18) which surrounds the balloon.

The slit or slits 17 need not be straight; for example, the edges 17a bounding the slit or slits can have a helical shape corresponding to that of the edges 9, 10 of marginal portions 7, 8 forming part of the sleeve 6 of FIGS. 14 and 15. It is normally preferred to provide the hose or sleeve 16 with two or three equidistant straight or helical slits 17.

In the embodiment of FIGS. 17 and 18, the length of the illustrated slit 17 exceeds the length of the balloon 2 to such an extent that the length of the slot portions extending beyond the distal and proximal ends of the balloon 2 is between 12.5 and 25 percent of the length of the balloon. This ensures that the hose or sleeve 16 can expand to a desired extent, preferably all the way between the ends 17b of each slit 17.

The catheter 1 of FIGS. 17 and 18 can employ an elastic jacket 15. This renders it possible to make the hose or sleeve 16 of a material which is sufficiently stiff to dislodge even the hardest region or regions of an occlusion but need not be very elastic because the elasticity of the jacket suffices to ensure reliable contraction of the sleeve 16 in immediate response to deflation of the balloon 2.

The drawing shows that the means for expanding the sleeve 6, the sleeve 6' with jacket 15 or the sleeve 16 is constituted by an inflatable and deflatable balloon 2. However, it is equally within the purview of the invention to provide other expanding means in addition to or in lieu of a balloon. For example, the catheter can comprise a basket-shaped mechanical expanding device in the form of a coil spring or another spring which can be shifted relative to the sleeve to move from a retracted position, in which the spring is mechanically compressed, to an extended position within the sleeve whereby the spring is free to expand and to thus expand the sleeve. When the spring is retracted toward the proximal end of the catheter, the sleeve is free to contract preparatory to extraction of the entire distal end from a body cavity. A jacket 15 can be used with advantage irrespective of whether the sleeve is to be expanded by a single balloon, by two or more balloons and/or by one or more springs. This renders it possible to employ a non-elastic sleeve 6 or 16 or a non-elastic inner section 6'.

The fact that the hose or sleeve 16 of FIGS. 17 and 18 develops widened slits 17 (FIG. 18) when the balloon 2 is inflated, and that (in the absence of a jacket 15) the occlusion comes in direct contact with the balloon between the edges 17a of each expanded or widened slit 17 is of no consequence because any hard region 5 which is not shifted radially outwardly by the non-slotted portion of the sleeve 16 can be dislodged and moved toward the internal surface of the blood vessel or another part of a human body upon deflation of the balloon 2, angular displacement of the balloon and sleeve 16, and renewed inflation of the balloon.

It will be appreciated that FIGS. 17 and 18 show the hose or sleeve 16 on a greatly enlarged scale. In actual practice, the diameter of the sleeve 16 is so small that the width of a slit 17 between the edges 17a of a sleeve 16 which surrounds an inflated balloon 2 (FIG. 18) is much too small to permit a medium-sized or even a small hard region 5 of an occlusion to penetrate through the widened slit 17 and into deforming engagement with the adjacent portion of the inflated balloon 2. By the same token, the width of the expanded slit or slits 17 is not sufficient to permit outward penetration of a portion of the inflated balloon 2. In most or practically all instances, the edges 17a bounding an expanded or widened slit 17 of the sleeve 16 will intercept a hard region 5 of the occlusion, and such edges will also intercept the adjacent portion of the inflated balloon 2 if such portion of the balloon tends to penetrate through the slit 17 and into engagement with the material of an occlusion 3.

If the catheter of FIGS. 17 and 18 employs an elastic jacket 15 which surrounds the sleeve 16, hard regions of an occlusion are positively prevented from directly contacting the inflated balloon 2, and such balloon is prevented from expanding into direct contact with a portion of an occlusion. Moreover, the jacket 15 (if used in the catheter of FIGS. 17–18) will prevent the edges 17a from scraping any material off an occlusion during expansion or contraction of the sleeve 16 as well as during introduction of the distal end of the catheter into or during its extraction from a body cavity.

If the introduction of the distal end of the catheter into a blood vessel or into another part of an animal body, as well as the opening of one or more occlusions, is monitored on a screen, the person in charge can ascertain whether or not a single inflation of the balloon 2 suffices to uniformly expand each occlusion which surrounds the sleeve 16. If this is the case, the catheter can be withdrawn after a single inflation of the balloon 2. However, if the monitor indicates that one or more relatively hard regions of one or more occlusions (partly opened occlusions) are not sufficiently close to the adjacent wall of the blood vessel, the balloon is deflated, the distal end is turned about its axis, and the balloon is reinflated to ensure that the non-displaced hard region or regions are shifted radially outwardly in order to guarantee that the opened occlusion exhibits a smooth internal surface.

The presently preferred expanding means of the improved catheter is a balloon which can be inflated with a hydraulic or pneumatic fluid. However, the aforementioned mechanical expanding means can be used with similar advantage, either in lieu of or together with a balloon. The presently preferred mechanical expanding means is a spring having a basket-shaped end which can be introduced with a wire or the like by advancing through the carrier 1a in order to expand as soon as it enters the space within the contracted sleeve and to thus enlarge the sleeve into optimal engagement with the surrounding occlusion or occlusions. The sleeve is then located in such position that it can receive the advancing spring or springs as soon as such spring or springs are caused to move beyond the carrier and into the interior of the sleeve which is ready to be expanded in the interior of the surrounding occlusion or occlusions. Alternatively, the mechanical expander can include a suitable spindle which is to be rotated in order to advance in the carrier and to expand the sleeve at the distal end of the catheter subsequent to introduction of the sleeve into one or more occlusions. Contraction of the sleeve can be induced by withdrawing the spring or the spindle or automatically as soon as the spring or spindle is retracted. Contraction of the sleeve can also be initiated by moving the sleeve axially relative to the spring or spindle and/or vice versa.

The improved catheter is susceptible of many additional modifications. For example, the features of the catheter of FIGS. 1–8 can be combined with those of the catheter embodying the structure of FIG. 9, FIG. 10, FIG. 11, FIGS. 12–13, FIGS. 14–15, FIG. 16 or FIGS. 17–18; the features of the catheter embodying the structure of FIG. 9 can be combined with those of the catheter of FIG. 10, FIG. 11, FIGS. 12–13, FIGS. 14–15; FIG. 16 or FIGS. 17–18; and so forth.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A catheter having a proximal end and a distal end insertable into a body cavity, said distal end comprising an at least partly elastic scroll-shaped sleeve expansible from a smaller diameter for introduction into an occlusion in a body cavity to a larger diameter to thereby open the occlusion, said sleeve including an inner marginal portion and an outer marginal portion overlying said inner marginal portion at least in contracted condition of the sleeve, at least one of said marginal portions moving relative to the other of said marginal portions in the circumferential direction of said sleeve during expansion and contraction of the sleeve and said marginal portions having a helical shape, said sleeve tending to contract to said smaller diameter to thus facilitate extraction from the body cavity upon completed opening of the occlusion and said sleeve exhibiting a stiffness sufficient to resist localized deformation by an occlusion during expansion in the occlusion; and means for expanding said sleeve upon completion of introduction into an occlusion.

2. The catheter of claim 1, wherein said expanding means comprises an inflatable balloon in said sleeve.

3. The catheter of claim 1, wherein said expanding means comprises an inflatable balloon in said scroll-shaped sleeve, said inner marginal portion being connected to said balloon.

4. The catheter of claim 1, further comprising an elongated carrier extending from said proximal end toward said distal end, and means for connecting one of said marginal portions to said carrier.

5. The catheter of claim 1, wherein said marginal portions barely overlap or are closely adjacent each other and define a narrow clearance in expanded condition of said sleeve.

6. The catheter of claim 1, wherein said sleeve has a predetermined circumferential length in the contracted condition thereof and comprises a convoluted sheet having a width between said marginal portions in the range of between 125 and 300% of said circumferential length.

7. The catheter of claim 1, wherein said sleeve has an external surface and at least that portion of said sleeve which is adjacent said external surface consists of a friction-reducing material.

8. The catheter of claim 1, wherein said sleeve includes an inner section and an elastic jacket surrounding said inner section.

9. The catheter of claim 1, wherein said sleeve has at least one substantially circumferentially extending weakened portion to facilitate flexing of the sleeve.

* * * * *